United States Patent [19]

Zhang et al.

[11] Patent Number: 6,110,745

[45] Date of Patent: Aug. 29, 2000

[54] PREPARATION OF LIPID-NUCLEIC ACID PARTICLES USING A SOLVENT EXTRACTION AND DIRECT HYDRATION METHOD

[75] Inventors: Yuan-Peng Zhang, Mountain View, Calif.; Peter Scherrer; Michael J. Hope, both of Vancouver, Canada

[73] Assignee: Inex Pharmaceuticals Corp., Burnaby, Canada

[21] Appl. No.: 09/122,622

[22] Filed: Jul. 23, 1998

Related U.S. Application Data

[60] Provisional application No. 60/072,656, Jul. 24, 1997.

[51] Int. Cl.[7] .......................... C12N 15/88; A61K 9/127; A61K 48/00; B01J 13/02; B01J 13/04; C07H 21/04

[52] U.S. Cl. .................. 435/458; 435/91.1; 435/91.31; 435/325; 435/320.1; 424/93.2; 424/450; 264/4.1; 935/52; 935/54; 536/23.1; 536/24.5; 514/44

[58] Field of Search ................. 435/320.1, 93.1; 536/23.1, 24.5; 264/4.1; 514/44; 424/450, 423, 19

[56] References Cited

U.S. PATENT DOCUMENTS

| | | | |
|---|---|---|---|
| 5,283,185 | 2/1994 | Epand et al. | 435/458 |
| 5,705,385 | 1/1998 | Bally et al. | 435/320.1 |

FOREIGN PATENT DOCUMENTS

WO9640964  12/1996  WIPO ................. C12N 15/88

OTHER PUBLICATIONS

Andrea D. Branch, A good antisense molecule is hard to find, TIBS, 47–48, Feb. 1998.

Trisha Gura, Antisense Has Growing Pains, Science, pp. 575–577, Oct. 1995.

Stanley Crooke, Antisense '97: A roundtable on the state of the industry, Nature Biotechnology, p. 522, Jun. 1997.

Stanley Crooke, Antisense Research and Applications, Chapter 1, Basic Principles of Antisense Therapeutics, Springer–Verlag Press, Berlin, Heidelberg, New York, p. 3, Jul. 1998.

Chonn, et al., *Current Opinion in Biotechnology*, 6(6):698–708 (1995).

*Primary Examiner*—Robert A. Schwartzman
*Assistant Examiner*—Janet Epps
*Attorney, Agent, or Firm*—Townsend and Townsend and Crew LLP

[57] ABSTRACT

This invention relates to a novel Solvent Extraction and Direct Hydration (SEDH) method for preparing lipid-nucleic acid particles which are useful for the introduction of nucleic acids (e.g., plasmid DNA, antisense molecules, ribozymes, etc.) into cells. The lipid-nucleic acid particles prepared using the methods of the present invention have enhanced circulation characteristics and serum stability and, thus, they are extremely effective as nucleic acid delivery vehicles.

52 Claims, 9 Drawing Sheets

TABLE I.A

RIBOZYME (R5358.15) FORMULATIONS USING THE SOLVENT EXTRACTION/HYDRATION METHOD

| FORMULATION | BUFFER | DODAC/EPC/PEG-C14 MOLAR RATIO | OLIGO (μg) | LIPID/OLIGO w/w | LIPID/OLIGO (+/-) | SIZING RESULTS PARTICLE | SIZING RESULTS VESICLE | $x^2$ | ASSOC.(%) | DEAE COLUMN LIPID (%) | DEAE COLUMN OLIGO (%) | DEAE COLUMN ENCAP. (%) |
|---|---|---|---|---|---|---|---|---|---|---|---|---|
| AU13R232 | HBS 1 mL | 45:45:10 | 100 | 5.7 | 1:1 | 71±37 | 158±82 | 1.9 | 56.8 | 88.4 | 54.8 | 64.5 |
| AU15R241 | HBS 0.5 mL | 45:45:10 | 500 | 5.7 | 1:1 | 338±216 | 516±328 | 3 | 63.9 | n/a | 81.8 | 51.8 |
|  | HBS 2 mL |  | 600 |  |  | 299±190 | 468±309 | 3.5 | 83.9 | n/a | 61.8 | 61.8 |
|  | SONICATED 10SEC P2 |  |  |  |  | 140 | 250 |  | 51.1 | n/a | 83.5 | 63.5 |
| AU13R233 | HBS 1 mL | 45:45:10 | 100 | 11.4 | 2:1 | 78±40 | 167±84 | 1.5 | 73.3 | 94.7 | 45.98 | 45.98 |
| AU13R231 | HBS 1 mL | 45:45:10 | 20 | 17.1 | 3:1 | 74.9±44.7 | 213±127 | 6.2 | 66.2 | n/a | 64.8 | 64.8 |
|  | SONICATED 10SEC P2 |  |  |  |  | n/a | 159±84 | 14.7 | | | | |
| AU13R234 | HBS 1 mL | 47.5:47.5:5 | 100 | 9.6 | 2:1 | 122±53 | 244±125 | 5.3 | 92.6 | 93.78±1.7 | 83.2±12.3 | 88.7±11.5 |
| EXTRUDED 5 TIMES 100 nm | (02% OLIGO & 74% LIPID RCVY) | | | | | 72±36 | 143±58 | 0.5 | n/a | 72.9 | 72.47 | 99.4 |
| AU13R236 | HBS 1 mL | 90:0:10 | 100 | 5.2 | 2:1 | 67±41 | 209±131 | 13 | 100 | 88.4 | 76.6 | 85.5 |
| AU15R242 | HBS 3 mL | 90:0:10 | 1000 | 5.2 | 2:1 | >2000 AGGREGATED |  |  |  |  |  |  |

FIG. 7. (PAGE 1 OF 3)

TABLE 1.B

ANTISENSE (ISIS1082) FORMULATIONS USING THE SOLVENT EXTRACTION/HYDRATION METHOD

| FORMULATION | METHOD | DODAC/EPC/PEG-C14 MOLAR RATIO | OLIGO (μg) | LIPID/OLIGO (w/w) | (+/-) | SIZING RESULTS ||| DEAE COLUMN & OILGREEN ASSAY |||
|---|---|---|---|---|---|---|---|---|---|---|---|
| | | | | | | PARTICLE | VESICLE | $\chi^2$ | LIPID (%) | OLIGO (%) | ENCAP. (%) |
| AU21A251 | SEDH 1mL | 45:45:10 | 100 | 5.7 | 1:1 | 232±120 | 350±180 | 1.8 | n/a | n/a | n/a |
| | SONICATED 5 SEC P2 | | 100 | 5.7 | 1:1 | 135±58 | 221±95 | 0.6 | n/a | n/a | n/a |
| | SONICATED 10 SEC P2 | | 100 | 5.7 | 1:1 | 103±44 | 174±75 | 3.6 | 69.6 | 56.2 | 94.4 |
| AU21A261 | SEDH 1mL | 45:45:10 | 100 | 5.7 | 1:1 | 73.3±41 | 188±108 | 1 | 83.7 | 89.8 | 100 |
| AU21A282 | SEDH 1mL | 85:0.0:15 | 100 | 3.1 | 1:1 | 455±350 | 734±561 | 187 | n/a | n/a | n/a |
| | | DODAC/DOPE/PEG-C14 | | | | | | | | | |
| JL4A341 | HBS 1 mL | 45:45:10 | 100 | 11.4 | 2:1 | 154±103 | 305±175 | 0.3 | n/a | n/a | n/a |
| | SONICATED 20 SEC P2 | | | | | 142±81.5 | n/a | 4 | 83.2 | n/a | 78 |
| JL4A342 | HBS 1 mL | 25:65:10 | 100 | 21.3 | 2:1 | 310±158 | 404±206 | 0.5 | n/a | n/a | n/a |
| | SONICATED 20 SEC P2 | | | | | 145±75 | 273±141 | 0.6 | 63.5 | n/a | 53 |

FIG. 7. (PAGE 2 OF 3)

TABLE 1.C

PLASMID FORMULATIONS USING THE SOLVENT EXTRACTION/HYDRATION METHOD

| FORMULATION | METHOD | DODAC/EPC/PEG-C14 MOLAR RATIO | DNA (μg) | LIPID/DNA (w/w) | (+/-) | SIZING RESULTS | | | | DEAE COLUMN | | |
|---|---|---|---|---|---|---|---|---|---|---|---|---|
| | | | | | | PARTICLE | VESICLE | $x^2$ | ASSOC (%) | LIPID (%) | DNA (%) | ENCAP (%) |
| AU18C171 | SEDH 1mL | 45:45:10 | 100 | 5.7 | 1:1 | 275±144 | 387±202 | 4.5 | 88.6 | 57.9 | 51 | 58 |
| EXTRUDED 5 X 100 NM | RECOVERY 57% LIPID, 46% DNA | | | | | 137±53 | 76±34 | 1 | | | | |
| AU19C171 | SEDH 1mL | 45:45:10 | 100 | 11.4 | 2:1 | 412±233 | 270±153 | 13 | 78.8 | 90.8 | 15.4 | 17 |
| SE8C231 | SEDH 1mL | 45:45:10 | 50 | 5.7 | 1:1 | | | 13 | | | | |
| | SON30SEC | | | | | 220±130 | 85 | | 84.7 | 24.4 | 13.5 | 55.3 |
| SE8C233 | SEDH (10%a) | 45:45:10 | 50 | 5.7 | 1:1 | | | | | | | |
| EXTRUDED 5 X 100 NM | RECOVERY 75% DNA | | | | | 160 | 90 | | | 80 | 67.5 | 75 |

FIG. 7. (PAGE 3 OF 3)

PREPARATION OF LIPID-NUCLEIC ACID PARTICLES USING A SOLVENT EXTRACTION AND DIRECT HYDRATION METHOD

This application claim the benefit under 35 USC 119(e) of U.S. application No. 60/072,656, filed Jul. 24 1997, the discloure of which is incorpated by reference.

FIELD OF THE INVENTION

This invention relates to a novel Solvent Extraction and Direct Hydration (SEDH) method for preparing lipid-nucleic acid particles which are useful for the introduction of nucleic acids (e.g., plasmid DNA, antisense molecules, nucleic acid catalysts (e.g., ribozymes), etc.) into cells. The lipid-nucleic acid particles prepared using the methods of the present invention have enhanced circulation characteristics and serum stability and, thus, they are extremely effective as nucleic acid delivery vehicles.

BACKGROUND OF THE INVENTION

The delivery of polynucleic acids, such as DNA, antisense molecules and ribozymes, into cells for therapeutic effects is of great interest in both science and biotechnology fields. Since all nucleic acids are subject to enzyme degradation when administrated in free form and most nucleic acids do not possess the attributes required for intercellular delivery, it is desirable to design efficient delivery systems in which nucleic acids are protected from enzyme degradation. One of the non-viral systems is the complexes formed from cationic lipid and with nucleic acids. This approach takes advantage of the fact that polynucleic acids (DNA, RNA, antisense or ribozyme) are negatively charged molecules and can interact strongly with cationic molecules to form complexes. Other examples of such interactions are DNA condensation agents, such as poly-lysine, ethanol, lipopolyamines and $Ca^{++}$ precipitation. However, these systems are not appropriate for intracellular or venous injection.

It has previously been demonstrated that hydrophobic DNA can be extracted into organic solvents through electrostatic interactions with a variety of mono- and polycationic lipids, including DODAC, DDAB and lipofectamine, and the resulting hydrophobic complexes are stable in organic solvents (see, Bally, et al., *Adv. Drug Del. Rev.*, in press, 1997; Reimer, et al., *Biochemistry*, 34:12877–12883 (1995); and Wong, et al., *Biochemistry*, 35:5776–5763 (1996)). FIG. 1 illustrates the principle of the extraction of nucleic acids into the solvent phase in the presence of cationic lipids and the formation of hydrophobic complexes.

In the past, an attempt to form homogenous plasmid DNA-lipid particles by removing solvent has not been readily successful mainly because of severe aggregation of the DNA-lipid complexes or the adherence of the DNA-lipid complexes to the glass tubes. However, methods based on detergent dialysis have been successful for the preparation of small, homogeneous and stable plasmid DNA-lipid particles (see, International Publication No. WO 96/40964, the teachings of which are incorporated herein by reference). Such methods can also be used for the preparation of antisense oligonucleotides; however, excess cationic lipids are required to achieve significantly high encapsulation efficiency. Attempts to use the detergent dialysis method for the preparation of ribozyme formulation have, however, yielded lower encapsulation efficiency (<30%), probably due to the existence of secondary structure of ribozyme molecules. As such, the preparation of ribozyme formulations having higher encapsulation efficiencies remains a challenge.

Although previously developed detergent dialysis methods have successfully been used to form numerous lipid-nucleic acid particles, it would be advantageous to have additional methods which give high encapsulation efficiencies of nucleic acids (60–100%) at relatively low lipid-nucleic acid ratio. Quite surprisingly, the present invention provides such methods.

SUMMARY OF THE INVENTION

The present invention provides a novel Solvent Extraction and Direct Hydration (SEDH) method for the preparation of lipid-nucleic acid particles for the delivery of nucleic acids, such as antisense moleucles, nucleic acid catalysts (e.g., ribozymes) and plasmid DNAs, into cells for both therapeutic and non-therapeutic purposes. The SEDH method generally involves the generation of hydrophobic nucleic acids complexes with cationic lipids in an organic solvent together with non-cationic lipids and, preferably, PEG-containing lipids. Following the removal of the solvent, the lipid-nucleic acid particles are prepared by direct hydration of the lipid-nucleic acid complexes with, for example, a buffer. The resulting lipid-nucleic acid particles have enhanced circulation characteristics and are stable in aqueous solutions and serum. The sizes of the resulting lipid-nucleic acid particles are in the range of 200-500 nm, but can readily be reduced to about 50–150 nm by, for example, brief sonication. The SEDH method of the present invention is simple and time efficient. Moreover, the SEDH method of the present invention is extremely advantageous over existing methods because a high encapsulation efficiency of nucleic acids (60–100%) can be achieved with relatively low lipid-nucleic acid ratio. Such methods are particularly useful for the formulation of ribozymes and other catalytic nucleic acids.

More particularly, in one embodiment, the present invention provides a SEDH method for preparing a lipid-nucleic acid particle, the method comprising: (a) contacting a nucleic acid with a solution comprising a non-cationic lipid and a cationic lipid to form a lipid-nucleic acid mixture, the solution comprising about 15–35% water and about 65–85% of an organic solvent; (b) removing the aqueous portion of the lipid-nucleic acid mixture to form a non-aqueous lipid-nucleic acid mixture; (c) removing the organic solvent portion from the non-aqueous lipid-nucleic acid mixture to form a lipid-nucleic acid complex; and (d) hydrating the lipid-nucleic acid complex to form the nucleic acid-lipid particle. In a presently preferred embodiment, the solution includes a polyethyleneglycol (PEG)-lipid conjugate and, in particular, a PEG-Ceramide (PEG-Cer) conjugate. In another preferred embodiment, the solution further includes cholesterol.

In another embodiment, the present invention provides lipid-nucleic acid particles prepared by the above SEDH method, and in vivo and in vitro methods using such lipid-nucleic acid particles for the delivery of nucleic acids, such as antisense molecules, nucleic acid catalysts (e.g., ribozymes), plasmid DNAs, and other catalytic nucleic acids, into cells for therapeutic purposes. In one embodiment, the present invention relates to compositions for delivering nucleic acid catalysts to a cell, the composition comprising a lipid, a polyethyleneglycol-lipid (PEG-lipid) conjugate and a nucleic acid catalyst. In a presently preferred embodiment, the composition comprises a non-cationic lipid, a cationic lipid, a polyethyleneglycol-lipid (PEG-lipid) conjugate and a nucleic acid catalyst.

In another embodiment, the present invention relates to lipid-nucleic acid particles (e.g., lipid-nucleic acid catalyst particles), the lipid-nucleic acid particles comprising a nucleic acid encapsulated in a lipid composition, the lipid composition comprising a first lipid component and a second lipid component, wherein the first lipid component is a lipid having a substantially positive charged headgroup at a pH above 3 and the second lipid component is a PEG-lipid conjugate. In a presently preferred embodiment, greater than 10% of the dosage of lipid-nucleic acid particles remains in circulation 1 hour after intravenous administration in a mammal. In an even more preferred embodiment, greater than 20% of the dosage of lipid-nucleic acid particles remains in circulation 1 hour after intravenous administration in a mammal. In a preferred embodiment, the lipid-nucleic acid particles deliver a pharmaceutically effective amount of the nucleic acid to a disease site in a mammal which is distal to the site of administration of the lipid-nucleic acid particles in the mammal. Preferably, the disease site is selected from the group consisting of a neoplasia, a site of inflammation and a site of infection.

Other features, objects and advantages of the invention and its preferred embodiments will become apparent from the detailed description which follows.

DETAILED DESCRIPTION OF THE INVENTION AND PREFERRED EMBODIMENTS

Figure 1:
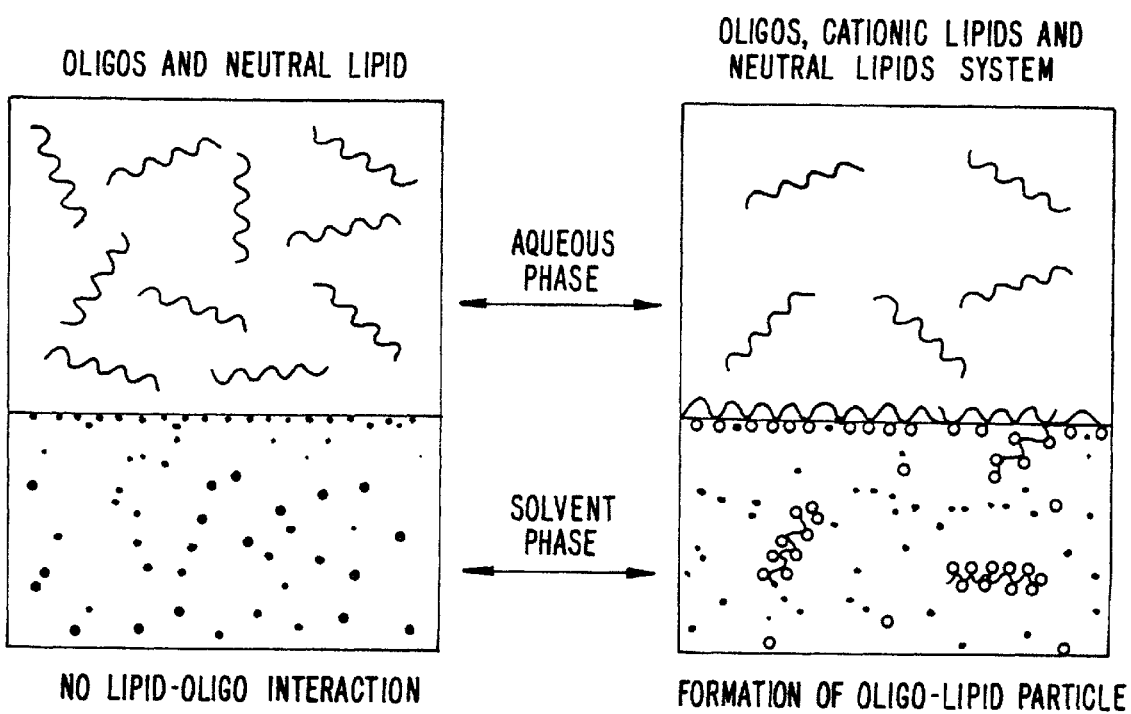
FIG. 1. Diagram illustrating the mechanism of polynucleic acids being extracted into the cationic lipid containing solvent phase and the resulted hydrophobic lipid/polynucleic acid complexes.

Table of Contents
I. Glossary
II. General
III. Methods of Formulating Lipid-Nucleic Acid Complexes and Particles
IV. Pharmaceutical Preparations
V. Administration of Lipid-Nucleic Acid Particle Formulations
VI. Examples

I. Glossary
A. Abbreviations and Definitions

The following abbreviations are used herein: CHO, Chinese hamster ovary cell line; B16, murine melanoma cell line; DC-Chol, 3$\beta$-(N-(N',N'-dimethylaminoethane) carbamoyl)cholesterol (see, Gao, et al., *Biochem. Biophys. Res. Comm.*, 179:280–285 (1991)); DDAB, N,N-distearyl-N,N-dimethylammonium bromide; DMRIE, N-( 1,2-dimyristyloxyprop-3-yl)-N,N-dimethyl-N-hydroxyethyl ammonium bromide; DODAC, N,N-dioleyl-N,N-dimethylammonium chloride (see, commonly owned patent application U.S. Ser. No. 08/316,399, incorporated herein by reference); DOGS, diheptadecylamidoglycyl spermidine; DOPE, 1,2-sn-dioleoylphoshatidylethanolamine; DOSPA, N-(1-(2,3-dioleyloxy)propyl)-N-(2-(sperminecarboxamido) ethyl)-N,N-dimethylammonium trifluoroacetate; DOTAP, N-(1-(2,3-dioleoyloxy)propyl)-N,N,N-trimethylammonium chloride; DOTMA, N-( 1-(2,3-dioleyloxy)propyl)-N,N,N-trimethylammoniumchloride; ESM, egg sphingomyelin; RT, room temperature; TBE, Tris-Borate-EDTA (89 mM in Tris-borate and 2 mM in EDTA); HEPES, 4-(2-hydroxyethyl)-1-piperazineethanesulfonic acid; PBS, phosphate-buffered saline; EGTA, ethylenebis (oxyethylenenitrilo)-tetraacetic acid.

The term "acyl" refers to a radical produced from an organic acid by removal of the hydroxyl group. Examples of acyl radicals include acetyl, pentanoyl, palmitoyl, stearoyl, myristoyl, caproyl and oleoyl.

As used herein, the term "pharmaceutically acceptable anion" refers to anions of organic and inorganic acids which provide non-toxic salts in pharmaceutical preparations. Examples of such anions include chloride, bromide, sulfate, phosphate, acetate, benzoate, citrate, glutamate, and lactate. The preparation of pharmaceutically acceptable salts is described in Berge, et al., *J. Pharin. Sci.*, 66:1–19 (1977), incorporated herein by reference.

The term "lipid" refers to any suitable material resulting in a bilayer such that a hydrophobic portion of the lipid material orients toward the bilayer while a hydrophilic portion orients toward the aqueous phase. Amphipathic lipids are necessary as the primary lipid vesicle structural element. Hydrophilic characteristics derive from the presence of phosphato, carboxylic, sulfato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group(s). The preferred amphipathic compounds are phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine could be used. Other compounds lacking in phosphorus, such as sphingolipid and glycosphingolipid families are also within the group designated as lipid. Additionally, the amphipathic lipids described above may be mixed with other lipids including triglycerides and sterols.

The term "neutral lipid" refers to any of a number of lipid species which exist either in an uncharged or neutral zwitterionic form at physiological pH. Such lipids include, for example diacylphosphatidylcholine, diacylphosphatidylethanolamine, ceramide, sphingomyelin, cephalin, and cerebrosides.

The term "non-cationic lipid" refers to any neutral lipid as described above as well as anionic lipids. Examples of anionic lipids include cardiolipin, diacylphosphatidylserine and diacylphosphatidic acid.

The term "cationic lipid" refers to any of a number of lipid species which carry a net positive charge at physiological pH. Such lipids include, but are not limited to, DODAC, DOTMA, DDAB, DOTAP, DC-Chol and DMRIE. Additionally, a number of commercial preparations of cationic lipids are available which can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA).

The term "nucleic acid catalyst" or, alternatively, "enzymatic nucleic acid molecule" is used herein to refer to a nucleic acid molecule capable of catalyzing (i.e., altering the velocity and/or rate of) a variety of reactions including the ability to repeatedly cleave other separate nucleic acid molecules (endonuclease activity) in a nucleotide base sequence-specific manner. Such a molecule with endonuclease activity may have complementarity in a substrate binding region to a specified gene target, and also has enzymatic activity that specifically cleaves RNA or DNA in that target. That is, the nucleic acid molecule with endonuclease activity is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention. The nucleic acids may be modified at the base and/or phosphate groups. The term enzymatic nucleic acid is used interchangeably with the following phrases: ribozymes, catalytic RNA, enzymatic RNA, catalytic DNA, catalytic oligonucleotides, nucleozyme, DNAzyme, RNA enzyme, endoribonuclease, endonuclease, minizyme, leadzyme, oligozyme or DNA enzyme. All of these terms describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving activity to the molecule. Numerous nucleic acid catalysts are described in U.S. patent application Ser. No. 09/122,588, filed on an even date herewith and bearing Attorney Docket No. 16303-005310, the teachings of which are incorporated herein by reference.

By "enzymatic portion" or "catalytic domain" is meant that portion/region of the ribozyme essential for cleavage of a nucleic acid substrate.

By "substrate binding arm" or "substrate binding domain" is meant that portion/region of a ribozyme which is complementary to (i.e., able to base-pair with) a portion of its substrate. Generally, such complementarity is 100%, but can be less if desired. For example, as few as 10 bases out of 14 may be base-paired. That is, the arms of the ribozymes contain sequences within a ribozyme which are intended to bring ribozyme and target together through complementary base-pairing interactions. The ribozyme of the invention may have binding arms that are contiguous or non-contiguous and may be varying lengths. The length of the binding arm(s) are preferably greater than or equal to four nucleotides; specifically 12–100 nucleotides; more specifically 14–24 nucleotides long. If a ribozyme with two binding arms are chosen, then the length of the binding arms are symmetrical (i.e., each of the binding arms is of the same length; e.g., six and six nucleotides or seven and seven nucleotides long) or asymmetrical (i.e., the binding arms are of different length; e.g., six and three nucleotides or three and six nucleotides long).

By "nucleic acid molecule" as used herein is meant a molecule having nucleotides. The nucleic acid can be single, double or multiple stranded and may comprise modified or unmodified nucleotides or non-nucleotides or various mixtures and combinations thereof. An example of a nucleic acid molecule according to the invention is a gene which encodes for macromolecule such as a protein.

By "complementarity" as used herein is meant a nucleic acid that can form hydrogen bond(s) with other nucleic acid sequence by either traditional Watson-Crick or other non-traditional types (for example, Hoogsteen type) of base-paired interactions.

The term "transfection" as used herein, refers to the introduction of polyanionic materials, particularly nucleic acids, into cells. The term "lipofection" refers to the introduction of such materials using liposome complexes. The polyanionic materials can be in the form of DNA or RNA which is linked to expression vectors to facilitate gene expression after entry into the cell. Thus, the polyanionic material used in the present invention is meant to include DNA having coding sequences for structural proteins, receptors and hormones, as well as transcriptional and translational regulatory elements (i.e., promoters, enhancers, terminators and signal sequences) and vector sequences. Methods of incorporating particular nucleic acids into expression vectors are well known to those of skill in the art, but are described in detail in, for example, Sambrook, et al., *Molecular Cloning: A Laboratory Manual* (2nd ed.), Vols. 1–3, Cold Spring Harbor Laboratory, (1989) or *Current Protocols in Molecular Biology*, F. Ausubel, et al., ed. Greene Publishing and Wiley-Interscience, New York (1987), both of which are incorporated herein by reference.

"Expression vectors", "cloning vectors", or "vectors" are often plasmids or other nucleic acid molecules that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

The term "hydrophobic" as applied to DNA and DNA complexes, refers to complexes which are substantially more soluble in organic solvents than in aqueous solutions. More particularly, hydrophobic DNA and DNA complexes are those which are at least 50% soluble in organic solvents such as chloroform/methanol mixtures, and preferably more than 70% soluble, more preferably more than 90% soluble in such organic solvents.

II. General Overview

The present invention provides a novel Solvent Extraction and Direct Hydration (SEDH) method for the preparation of lipid-nucleic acid particles for the delivery of nucleic acids, such as antisense molecules, nucleic acid catalysts (e.g., ribozymes) and plasmid DNAs, into cells for both therapeutic and non-therapeutic purposes. The SEDH method generally involves the generation of hydrophobic nucleic acids complexes with cationic lipids in an organic solvent together with non-cationic lipids and, preferably, PEG-containing lipids and cholesterol. Following the removal of the solvent, the lipid-nucleic acid particles are prepared by direct hydration of the lipid-nucleic acid complexes with, for example, a buffer. The resulting lipid-nucleic acid particles have enhanced circulation characteristics and are stable in aqueous solutions and serum. The sizes of the resulting lipid-nucleic acid particles are in the range of 200–500 nm, but can readily be reduced to about 50–150 nm by, for example, brief sonication. The SEDH method of the present invention is simple and time efficient. Moreover, the SEDH method of the present invention is extremely advantageous over existing methods because a high encapsulation efficiency of nucleic acids (60–100%) can be achieved with relatively low lipid-nucleic acid ratio. The SEDH method is useful for formulating plasmid DNA, antisense molecules and, in particular, ribozymes and other nucleic acid catalytsts.

In presently preferred embodiments, the lipid-nucleic acid particles of the present invention comprise a non-cationic lipid, a cationic lipid and a nucleic acid. In further preferred embodiments, the lipid-nucleic acid particles comprise a PEG-lipid conjugate and, in particular, a PEG-Cer conjugate. In a further preferred embodiment, the lipid nucleic acid particles comprise cholesterol. In still further preferred embodiments, the lipid-nucleic acid particles comprise both a PEG-lipid conjugate and cholesterol. The lipid-nucleic acid particles of the present invention can be used to effectively deliver a nucleic acid, e.g., plasmid DNA, an antisense molecule or a catalytic nucleic acid, to a cell or biological system for therapeutic purposes. As such, the present invention provides methods for delivering or introducing a nucleic acid into a target cell of interest for the treatment of various diseases, such as inflammation, cancer, tumor angiogenesis, infectious diseases, tumor metastasis and the like.

III. Methods of Forming Lipid-Nucleic Acid Complexes and Particles

The present invention provides a SEDH method for the preparation of lipid-nucleic acid particles. More particularly, in one embodiment, the present invention provides a SEDH method for preparing a lipid-nucleic acid particle, the method comprising: (a) contacting a nucleic acid with a solution comprising a non-cationic lipid and a cationic lipid to form a lipid-nucleic acid mixture, the solution comprising about 15–35% water and about 65–85% of an organic solvent; (b) removing the aqueous portion of the lipid-nucleic acid mixture to form a non-aqueous lipid-nucleic acid mixture; (c) removing the organic solvent portion from the non-aqueous lipid-nucleic acid mixture to form a lipid-nucleic acid complex; and (d) hydrating the lipid-nucleic acid complex to form the nucleic acid-lipid particle.

In the first step of the SEDH method, a nucleic acid is contacted with a solution comprising a non-cationic lipid and a cationic lipid to form a lipid-nucleic acid mixture, the solution comprising about 15–35% water and about 65–85% of an organic solvent. In a presently preferred embodiment, the solution also includes a polyethylene-glycol (PEG)-lipid conjugate and, in particular, a PEG-Ceramide (PEG-Cer) conjugate. In another preferred embodiment, the solution further includes cholesterol. In an even more preferred embodiment, the solution further includes a PEG-lipid conjugate and cholesterol.

Nucleic acids which are useful in the present invention are typically nucleotide polymers having from 10 to 100,000 nucleotide residues. Typically, the nucleic acids are to be administered to a subject for the purpose of repairing or enhancing the expression of a cellular protein for cleaving specific RNA targets within the background of cellular RNA, etc. Additionally, the nucleic acid can carry a label (e.g., a radioactive label, fluorescent label or colorimetric label) for the purpose of providing clinical diagnosis relating to the presence or absence of complementary nucleic acids. Accordingly, the nucleic acids, or nucleotide polymers, can be polymers of nucleic acids including genomic DNA, cDNA, niRNA or oligonucleotides containing nucleic acid analogs, for example, the antisense derivatives described in a review by Stein, et al., *Science*, 261:1004–1011 (1993) and in U.S. Pat. Nos. 5,264,423 and 5,276,019, the disclosures of which are incorporated herein by reference. Still further, the nucleic acids may encode transcriptional and translational regulatory sequences including promoter sequences and enhancer sequences.

The nucleotide polymers can be single-stranded DNA or RNA, or double-stranded DNA or DNA-RNA hybrids. Examples of double-stranded DNA include structural genes, genes including control and termination regions, and self-replicating systems such as plasmid DNA.

Single-stranded nucleic acids include antisense oligonucleotides (complementary to DNA and RNA), ribozymes, other catalytic nucleic acids and triplex-forming oligonucleotides. In order to increase stability, some single-stranded nucleic acids will preferably have some or all of the nucleotide linkages substituted with stable, non-phosphodiester linkages, including, for example, phosphorothioate, phosphorodithioate, phosphoroselenate or 0-alkyl phosphotriester linkages.

The nucleic acids used in the present invention will also include those nucleic acids in which modifications have been made in one or more sugar moieties and/or in one or more of the pyrimidine or purine bases. Examples of sugar modifications include replacement of one or more hydroxyl groups with halogens, alkyl groups, amines, azido groups or functionalized as ethers or esters. Additionally, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

Multiple genetic sequences can be also be used in the present methods. Thus, the sequences for different proteins may be located on one strand or plasmid. Promoter, enhancer, stress or chemically-regulated promoters, antibiotic-sensitive or nutrient-sensitive regions, as well as therapeutic protein encoding sequences, may be included as required. Non-encoding sequences may also be present to the extent that they are necessary to achieve appropriate expression.

The nucleic acids used in the present method can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester and H-phosphonate chemistries are widely available. See, for example, Itakura, U.S. Pat. No. 4,401,796; Caruthers, et al., U.S. Pat. Nos. 4,458,066 and 4,500,707; Beaucage, et al., *Tetrahedron Lett.,* 22:1859–1862 (1981); Matteucci, et al., *J. Am. Chem. Soc.,* 103:3185–3191 (1981); Caruthers, et al., *Genetic Engineering,* 4:1–17 (1982); Jones, chapter 2, Atkinson, et al., chapter 3, and Sproat, et al., chapter 4, in *Oligonucleotide Synthesis: A Practical Approach,* Gait (ed.), IRL Press, Washington D.C. (1984); Froehler, et al., *Tetrahedron Lett.,* 27:469–472 (1986); Froehler, et al., *Nucleic Acids Res.,* 14:5399–5407 (1986); Sinha, et al., *Tetrahedron Lett.,* 24:5843–5846 (1983); and Sinha, et al., *Nucl. Acids Res.,* 12:4539–4557 (1984) which are incorporated herein by reference.

The non-cationic lipids used in the methods and, in turn, the lipid-nucleic acid particles of the present invention can be any of a variety of neutral uncharged, zwitterionic or anionic lipids. Examples of non-cationic lipids which are useful in the present methods are diacylphosphatidylcholines, diacylphosphatidylethanolamines, ceramides, sphingomyelins, cephalins and cerebrosides. Other lipids, such as lysophosphatidylcholine and lysophosphatidylethanolamine, can also be present. In preferred embodiments, the non-cationic lipids are diacylphosphatidylcholines (e.g., dioleoylphosphatidylcholine, dipalmitoylphosphatidylcholine and dilinoleoylphosphatidylcholine), diacylphosphatidylethanolamine (e.g., dioleoylphosphatidylethanolamine and palmitoyloleoylphosphatidylethanolamine), ceramide or sphingomyelin. The acyl groups in these lipids are preferably acyl groups derived from fatty acids having $C_{10}$–$C_{24}$ carbon chains. More preferably, the acyl groups are lauroyl, myristoyl, palmitoyl, stearoyl or oleoyl. In particularly preferred embodiments, the non-cationic lipid will be a diacylphosphatidylcholine and, in particular, egg yolk phosphatidylcholine. Other non-cationic lipids known to and used by those of skill in the art can be used in the methods and lipid-nucleic acid particles of the present invention.

Examples of suitable cationic lipids include, but are not limited to, the following: DC-Chol, 3β-(N-(N',N'-dimethylaminoethane)carbamoyl)cholesterol (see, Gao, et al., *Biochem. Biophys. Res. Comm.,* 179:280–285 (1991); DDAB, N,N-distearyl-N, N-dimethylammonium bromide; DMRIE, N-(1,2-dimyristyloxyprop-3-yl)-N,N-dimethyl-N-hydroxyethyl ammonium bromide; DODAC, N,N-dioleyl-N,N-dimethylammonium chloride (see, commonly owned U.S. patent application Ser. No. 08/316,399, filed Sep. 30, 1994, which is incorporated herein by reference); DOGS, diheptadecylamidoglycyl spermidine; DOSPA, N-(1-(2,3-dioleyloxy) propyl)-N-(2-(sperminecarboxamido)ethyl)-N, N-dimethylammonium trifluoroacetate; DOTAP, N-(1 -(2,3-dioleoyloxy)propyl)-N, N ,N-trimethylammonium chloride; DOTMA, N-(1-(2,3-dioleyloxy)propyl)-N, N,N-trimethylammonium chloride;; LIPOFECTIN, a commercially available cationic lipid comprising DOTMA and DOPE (GIBCO/BRL, Grand Island, N.Y.) (U.S. Pat. Nos. 4,897,355; 4,946,787; and 5,208,036 issued to Epstein, et al.); LIPOFECTACE or DDAB (dimethyldioctadecyl ammonium bromide) (U.S. Pat. No. 5,279,883 issued to Rose); LIPOFECTAMINE, a commercially available cationic lipid composed of DOSPA and DOPE (GIBCO/BRL, Grand Island, N.Y.); TRANSFECTAM, a commercially available cationic lipid comprising DOGS (Promega Corp., Madison, Wis.). In a presently preferred embodiment, the cationic lipid is N,N-dioleyl-N,N- dimethylammonium chloride (DODAC) or 1,2-dioleoyloxy-3-(N,N,N-trimethylamino) propane chloride (DOTAP).

In addition to the non-cationic and cationic lipids, the solution and, in turn, the lipid-nucleic acid particles of the present invention preferably contain a polyethylene-glycol (PEG)-lipid conjugate. In a presently preferred embodiment, the PEG-lipid conjugate is a polyethyleneglycol conjugated to, i.e., coupled to, a phosphatidylethanolamine (PE). In an even more preferred embodiment, the PEG-lipid conjugate is a polyethyleneglycol conjugated to a ceramide (Cer). PEG can be conjugated to a phosphatidylethanolamine or, alternatively, to a ceramide using standard coupling reactions known to and used by those of skill in the art. Such linkages can be cleavable or non-cleavable. In addition, preformed polyethyleneglycol-phosphatidylethanolamine conjugates are commercially available from Avanti Polar Lipids (Alabaster, Ala.).

Polyethyleneglycols of varying molecular weights can be used to form the PEG-lipid conjugates of the present invention. Polyethyleneglycols of varying molecular weights are commercially available from a number of different sources or, alternatively, they can be synthesized using standard polymerization techniques well-known to those of skill in the art. In a presently preferred embodiment, the polyethylene glycol has a molecular weight ranging from about 200 to about 10,000, more preferably from about 1,000 to about 8,000, and even more preferably from about 2,000 to about 6,000. Generally, it has been found that increasing the molecular weight of the polyethyleneglycol reduces the concentration of the PEG-lipid conjugate required to achieve stabilization.

Phosphatidylethanolamines having a variety of acyl chain groups of varying chain lengths and degrees of saturation can be conjugated to polyethyleneglycol to form the PEG-lipid conjugate. Such phosphatidylethanolamines are commercially available, or can be isolated or synthesized using conventional techniques known to those of skill in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, the following: dimyristoylphosphatidylethanolamine (DMPE), dipalmitoylphosphatidylethanolamine (DPPE), dioleoylphosphatidylethanolamine (DOPE) and distearoylphosphatidyl-ethanolamine (DSPE).

As with the phosphatidylethanolamines, ceramides having a variety of acyl chain groups of varying chain lengths and degrees of saturation can be coupled to polyethyleneglycol to form the PEG-lipid conjugate. It will be apparent to those of skill in the art that in contrast to the phosphatidylethanolamines, ceramides have only one acyl group which can be readily varied in terms of its chain length and degree of saturation. Ceramides suitable for use in accordance with the present invention are commercially available. In addition, ceramides can be isolated, for example, from egg or brain using well-known isolation techniques or, alternatively, they can be synthesized using the methods and techniques disclosed in U.S. patent application Ser. No. 08/316,429, filed Sep. 30, 1994, and PCT Publication No. WO 96/10391, the teachings of which are incorporated herein by reference. Using the synthetic routes set forth in the foregoing applications, ceramides having saturated or unsaturated fatty acids with carbon chain lengths in the range of $C_2$ to $C_{31}$ can be prepared.

In a presently preferred embodiment, the solution and, in turn, the lipid-nucleic acid particle comprises a PEG-Cer conjugate. Preferably, the ceramide has a fatty acid group having between 6 and 24 carbon atoms. In particularly preferred embodiments, the PEG-Cer conjugate has fatty acid groups comprising 8, 14, or 20 carbon atoms, designated as PEG-Cer-C8 (or PEG-C8), PEG-Cer-C14 (or PEG-C14); and PEG-Cer-C20 (or PEG-C20), respectively.

The non-cationic lipid, the cationic lipid and, preferably, the PEG-lipid conjugate are combined in various proportions which allow for the effective delivery of the nucleic acid to a desired cell or biological system of interest (e.g., plasmid DNA, antisense molecules or ribozyme). Typically, the non-cationic lipid is present at a concentration ranging from about 20 mole percent to about 95 mole percent. More preferably, the non-cationic lipid is present at a concentration ranging from about 40 mole percent to about 60 mole percent. More preferably, the non-cationic lipid is present at a concentration of about 50 mole percent. The cationic lipid is typically present at a concentration ranging from about 5 mole percent to about 80 mole percent. More preferably, the cationic lipid is present at a concentration ranging from about 10 mole percent to about 40 mole percent. More preferably, the cationic lipid is present at a concentration of about 15 mole percent. If present, the PEG-lipid conjugate is typically present at a concentration ranging from about 0.5 mole percent to about 50 mole percent. More preferably, the PEG-lipid conjugate is present at a concentration ranging from about 5 mole percent to about 20 mole percent. More preferably, the PEG-lipid conjugate is present at a concentration of about 10 mole percent.

In a presently preferred embodiment, the solution and, in turn, the lipid-nucleic acid particles of the present invention further contain cholesterol. Cholesterol can be added, for example, to increase the thermal transition temperature of the composition in cases where it is necessary to increase the stability of the composition in a biological system and/or to reduce the rate of leakage of encapsulated enzymatic nucleic acid. Cholesterol, if included, is generally present at a concentration ranging from 0.02 mole percent to about 50 mole percent, more preferably, at a concentration ranging from about 15 mole percent to about 45 mole percent and, more preferably, at a concentration of about 25 mole percent.

Briefly, all of the components, e.g., the nucleic acid, the non-cationic lipid, the cationic lipid and, preferably, a PEG-lipid conjugate and, preferably, cholesterol, are codissolved in a solution, the solution preferably comprising about 15–35% water and about 65–85% of an organic solvent. The forming of the hydrophobic lipid nucleic acid complexes can be carried out in a monophase system (e.g., a Bligh and Dyer monophase or similar mixture of aqueous and organic solvents), or in a two phase system with suitable mixing. When formation of the complexes is carried out in a monophase system, all of the components are codissolved in the monophase mixture. Alternatively, the complexes can form in two-phase mixtures in which the cationic lipids bind to the nucleic acid (which is present in the aqueous phase), and "pull" it in to the organic phase.

Organic solvents suitable for use in the SEDH method of the present invention include, but are not limited to, the following: chloroform, dichloromethane, diethylether, cyclohexane, cyclopentane, benzene, toluene, acetone, benzyl alcohol, methanol, other aliphatic alcohols, such as propanol, isopropanol, butanol, tert-butanol, iso-butanol, pentanol and hexanol, or mixture thereof. The selection of an organic solvent will typically involve consideration of solvent polarity and the ease with which the solvent can be removed at the later stages of particle formation. Accordingly, the preferred organic solvents are ethanol, dichloromethane, chloroform, methanol, diethyl ether, or mixture thereof, with a methanol/chloroform mixture being the preferred organic solvent.

In a presently preferred embodiment, the various components are codissolved in a monophase of $MeOH/CHCl_3/H_2O$ to form a lipid-nucleic acid mixture. The various components can, if necessary, be mixed using any number of methods, such as by mechanical means using a vortex mixer. After an incubation of about 30 minutes, the aqueous portion of the lipid-nucleic acid mixture is substantially removed to form a non-aqueous lipid-nucleic acid mixture. Prior to removing the aqueous portion, it is desirable to add additional organic solvent (e.g., $CHCl_3$) and water so that a clear interface between the aqueous portion and the organic solvent portion forms after centrifugation.

After removal of the aqueous portion, the organic solvent portion is removed from the non-aqueous lipid-nucleic acid mixture to form a lipid-nucleic acid complex. Removal of the organic solvent portion is typically accomplished at reduced pressures or by blowing a stream of inert gas (e.g., nitrogen or argon) across the mixture. In a presently preferred embodiment, the non-aqueous lipid-nucleic acid mixture is subjected to gentle $N_2$ blow to remove the organic solvent portion while slowly rotating the container, e.g., test tube, so that a uniform film of lipid-nucleic acid complexes is formed.

After removal of the organic solvent portion, the lipid-nucleic acid particles are obtained from the uniform film of lipid-nucleic acid complexes by hydration. In a presently preferred embodiment, the lipid-nucleic acid complexes are hydrated with a buffer to form the lipid-nucleic acid complexes of the present invention. Suitable buffers include, but are not limited to, HEPES, PBS, EGTA, citrate, tris EDTA and tris buffer. In a presently preferred embodiment, a HBS buffer (20 mM HEPES, 150 mM NaCl, pH 7.2) is used to hydrate the lipid-nucleic acid complexes to form the lipid-nucleic acid particles.

The size of the resulting lipid-nucleic acid particle will typically be in the range of 200 to 500 microns. To achieve further size reduction or homogeneity of size in the particles, the lipid-nucleic acid particles can be sonicated, filtered or subjected to other sizing techniques which are used in liposomal formulations and are known to those of skill in the art. In a presently preferred embodiment, sonication is used to size the oligonucleotides (e.g., ribozymes and antisense molecules), whereas extrusion methods are used to size plasmid DNA.

The resulting lipid-nucleic acid particles have enhanced circulation characteristics and are stable in aqueous solutions and serum. Moreover, the above SEDH method is simple and time efficient. In addition, the SEDH method of the present invention is extremely advantageous over existing methods because a high encapsulation efficiency of nucleic acids can be achieved with a relatively low lipid-nucleic acid ratio. In a presently preferred embodiment, greater than 60% of the nucleic acid is encapsulated into the lipid-nucleic acid particle. In an even more preferred embodiment, greater than 70% of the nucleic acid is encapsulated into the lipid-nucleic acid particle. In an even more preferred embodiment, greater than 80% of the nucleic acid is encapsulated into the lipid-nucleic acid particle. In an even more preferred embodiment, greater than 90% of the nucleic acid is encapsulated into the lipid-nucleic acid particle. In an even more preferred embodiment, greater than 95% of the nucleic acid is encapsulated into the lipid-nucleic acid particle. Again, a high encapsulation efficiency of nucleic acids can be achieved with a relatively low lipid-nucleic acid ratio.

Once formed, the resulting lipid-nucleic acid particles can be use in in vivo and in vitro methods to deliver or introduce nucleic acids, such as antisense molecules, nucleic acid catalysts (e.g., ribozymes) and plasmid DNA, into cells for therapeutic purposes.

IV. Pharmaceutical Preparations

The lipid-nucleic acid particles of the present invention can be administered either alone or in combination with a physiologically-acceptable carrier (such as physiological saline or phosphate buffer) selected in accordance with the route of administration and standard pharmaceutical practice.

Pharmaceutical compositions comprising the lipid-nucleic acid particles of the invention are prepared according to standard techniques and further comprise a pharmaceutically acceptable carrier. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. In compositions comprising saline or other salt containing carriers, the carrier is preferably added following particle formation. Thus, after the particle is formed, the particle can be diluted into pharmaceutically acceptable carriers such as normal saline. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of particles in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration. For diagnosis, the amount of particlesused, the disease state being the particular label used, the disease state being diagnosed and the judgement of the clinician but will generally be between about 0.01 and about 50 mg per kilogram of body weight, preferably between about 0.1 and about 5 mg/kg of body weight.

As noted above, it is often desirable to include polyethylene glycol (PEG)-modified phospholipids, PEG-ceramide, or ganglioside GM,-modified lipids to the particles. Addition of such components prevents particle aggregation and provides a means for increasing circulation lifetime and increasing the delivery of the lipid-nucleic acid particles to the target tissues. Typically, the concentration of the PEG-modified phospholipids, PEG-ceramide or $G_{M1}$-modified lipids in the particle will be about 1–15%.

Overall particle charge is also an important determinant in particle clearance from the blood. Charged liposomes and particles are typically taken up more rapidly by the reticuloendothelial system (Juliano, *Biochem. Biophys. Res. Commun.*, 63:651 (1975)) and thus have shorter half-lives in the bloodstream. Particles with prolonged circulation half-lives are typically desirable for therapeutic and diagnostic uses. For instance, particles which can be maintained from 8, 12, or up to 24 hours in the bloodstream are particularly preferred.

In another example of their use, lipid-nucleic acid particles can be incorporated into a broad range of topical dosage forms including but not limited to gels, oils, emulsions and the like. For instance, the suspension containing the lipid-nucleic acid particles can be formulated and administered as topical creams, pastes, ointments, gels, lotions and the like.

The present invention also provides lipid-nucleic acid particles in kit form.

The kit will typically be comprised of a container which is compartmentalized for holding the various elements of the kit. The kit will contain the compositions of the present inventions, preferably in dehydrated form, with instructions for their rehydration and administration. In still other embodiments, the particles and/or compositions comprising the particles will have a targeting moiety attached to the surface of the particle. Methods of attaching targeting moieties (e.g., antibodies, proteins) to lipids (such as those used in the present particles) are known to those of skill in the art.

Dosage for the lipid-nucleic acid particle formulations will depend on the ratio of nucleic acid to lipid and the administrating physician's opinion based on age, weight, and condition of the patient.

V. Administration of Lipid-Nucleic Acid Particle Formulations

Following formation of the lipid-nucleic acid particles, the particles can be contacted with the cells to be transfected. The particles can be adsorbed to almost any cell type. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid. Contact between the cells and the lipid-nucleic acid particles, when carried out in vitro, will take place in a biologically compatible medium. The concentration of particles can vary widely depending on the particular application, but is generally between about 1 μmol and about 10 mmol. Treatment of the cells with the lipid-nucleic acid particles will generally be carried out at physiological temperatures (about 37° C.) for periods of time of from about 1 to 48 hours, preferably of from about 2 to 4 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mamtnalian cells, and most preferably human cells.

In one group of preferred embodiments, a lipid-nucleic acid particle suspension is added to 60–80% confluent plated cells having a cell density of from about $10^3$ to about $10^5$ cells/mL, more preferably about $2\times10^4$ cells/mL. The concentration of the suspension added to the cells is preferably of from about 0.01 to 0.2 μg/mL, more preferably about 0.1 μg/mL.

Typical applications include using well known transfection procedures to provide intracellular delivery of DNA or MRNA sequences which code for therapeutically useful polypeptides. However, the compositions can also be used for the delivery of the expressed gene product or protein itself. In this manner, therapy is provided for genetic diseases by supplying deficient or absent gene products (i.e., for Duchenne's dystrophy, see, Kunkel, et al., *Brit. Med. Bull.,* 45(3):630–643 (1989), and for cystic fibrosis, see, Goodfellow, *Nature,* 341:102–103 (1989)). Other uses for the compositions of the present invention include introduction of antisense oligonucleotides in cells (see, Bennett, et al., *Mol. Pharm.,* 41:1023–1033 (1992)).

Alternatively, the compositions of the present invention can also be used for the transfection of cells in vivo, using methods which are known to those of skill in the art. In particular, Zhu, et al., *Science,* 261:209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature,* 362:250–256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.,* 298:278–281 (1989), incorporated herein by reference, describes the in vivo transfection of lungs of mice with a functioning prokaryotic gene encoding the intracellular enzyme, chloramphenicol acetyltransferase (CAT).

For in vivo administration, the pharmaceutical compositions are preferably administered parenterally, i.e., intraarticularly, intravenously, intraperitoneally, subcutaneously, or intramuscularly. More preferably, the pharmaceutical compositions are administered intravenously or intraperitoneally by a bolus injection. For example, see, Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York, 101:512–527 (1983); Mannino, et al., *Biotechniques,* 6:682–690 (1988); Nicolau, et al., *Crit. Rev. Ther. Drug Carrier Syst.,* 6:239–271 (1989), and Behr, *Acc. Chem. Res.,* 26:274–278 (1993). Still other methods of administering lipid-based therapeutics are described in, for example, Rahman, et al., U.S. Pat. No. 3,993,754; Sears, U.S. Pat. No. 4,145,410; Papahadjopoulos, et al., U.S. Pat. No. 4,235,871; Schneider, U.S. Pat. No. 4,224,179; Lenk, et al., U.S. Pat. No. 4,522,803; and Fountain, et al., U.S. Pat. No. 4,588,578. The pharmaceutical compositions of the present invention can also be administered locally or, advantageously, systemically.

In other methods, the pharmaceutical preparations may be contacted with the target tissue by direct application of the preparation to the tissue. The application may be made by topical, "open" or "closed" procedures. By "topical," it is meant the direct application of the pharmaceutical preparation to a tissue exposed to the environment, such as the skin, oropharynx, external auditory canal, and the like. "Open" procedures are those procedures include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid particles can also be administered in an aerosol inhaled into the lungs (see, Brigham, et al., *Am. J. Sci.,* 298(4):278–281 (1989)) or by direct injection at the site of disease (Culver, HUMAN GENE THERAPY, MaryAnn Liebert, Inc., Publishers, New York. pp.70–71 (1994)).

The methods of the present invention may be practiced in a variety of hosts. Preferred hosts include mammalian species, such as humans, non-human primates, dogs, cats, cattle, horses, sheep, and the like.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

V. Examples

A. Materials

Cationic lipid, N,N-dioleyl-N$_2$N-dimethyl ammonium chloride (DODAC), and monomethoxy polyethylene$_{2000}$ glycol succinate-(C8:ceramide) (PEG-Cer-C8) were synthesized by Michael Feng/Steven Ansell and Zhao Wang, respectively, at Inex Pharmaceuticals Corp. pCMV CAT was also produced at Inex Pharmaceuticals Corp. Dioleylphosphatidylethanolamine (DOPE) and egg phosphatidylcholine (EPC) were supplied by Northern Lipids. OliGreen ssDNA and PicoGreen dsDNA quantitation reagents were supplied by Molecular Probes. Sodium Chloride, HEPES, Triton x-100 and Octyl-β-D-glucoside were obtained from VWR Scientific, Fisher Scientific or Sigma Chemical company. Antisense ISIS 1082, a phosphothioate antisense oligonucleotide, was obtained from ISIS Pharmaceuticals. Ribozyme, R5356.15 was obtained from Ribozyme Pharmaceuticals Incorporated. Sonifier (Model 250) was purchased from Branson Ultrasonic Corp. (Danbury, Conn.).

B. Methods

Figure 2:
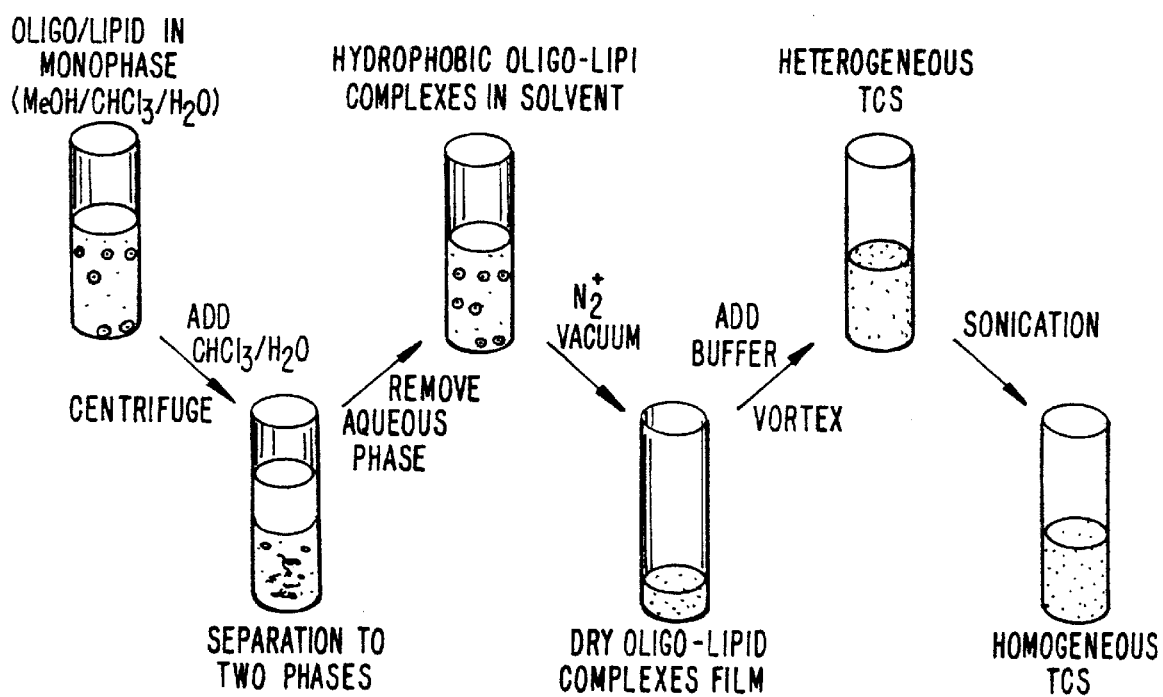
FIG. 2. Diagram illustrating the procedures of solvent extraction and direct hydration method for preparing oligo-lipid TCS.

The procedures for preparing lipid/polynucleic acid particles from hydrophobic lipid/nucleic acid complexes isolated in organic solvent are illustrated in FIG. 2. The following is a step-by-step description of the procedures.

1. Preparing hydrophobic lipid-oligo complexes in organic solvents All components, including cationic lipid, neutral lipids (EPC or DOPE), PEG-Cer-C14 and oligonucleotides, were codissolved in a monophase composed of MeOH/CHCl$_3$/H$_2$O(2:1:1 :1 v/v). After about 30 min. incubation at room temperature, additional CHCl$_3$ and H$_2$O (about ¼ of the original volume each) were added. After centrifugation at 3000 rpm for 10 min. using a bench type centrifuge, a clear interface between the aqueous and the solvent phase was formed.

2. Making Hydrophobic Lipid-nucleic Acid Complexes as Dry Films

After removing the upper aqueous phase, the solvent phase was subjected to gentle N$_2$ blow to remove the solvent while slowly rotating the test tube so that a uniform film of lipid nucleic acid complexes was formed. The sample was then placed under vacuum for at least 3 hours.

3. Preparing Lipid-oligo Formulation by Hydration

A sufficient volume of HBS buffer (20 mM HEPES, 150 mM NaCl, pH 7.2) was added to the lipid film obtained in the last step followed by hard vertexing until all material on the test tube wall was removed and a homogeneous formulation was obtained. Both heating (up to 40° C. for plasmid, and 60° C. for oligonucleotides) and sonication of the formulation, if oligonucleotides were used, in a bath sonicator will help this process.

4. Measurement of Formulation Size Distribution

The size distributions of formulations were measured using a NICOMP particle sizer. Gaussian and NICOMP distributions in both solid particles and vesicle modes were recorded (see, FIG. 4).

5. Reduction of Lipid-nucleic Acid TCS Sizes a. Oligonucleotides (antisenses and ribozymes)

Because both antisenses and ribozymes are stable upon sonication (see, FIG. 4), sonication can be used to reduce the size of oligonucleotide particles. For instance, sonication of an antisense formulation [DODAC/EPC/PEG-C14 (45:45:10), ±: 1:1] for 10 seconds at low power (position 1) reduced the particle size to 103 nm from 232 nm (see, FIG. 5).

b. Plasmid DNA

Although plasmid DNA in lipid-DNA particles can sustain short period sonication, long time sonication is normally required to reduce the particle size to an acceptable value. Extrusion was used to decrease the particle size. However, the recovery of formulation through extortion process (5 times through 0.1 μm two stacked filter) has been low (45–65%, see, formulations AU19C171 and AU13R234 in Table 1).

The addition of appropriate amount of ethanol into the formulation helped the recovery of DNA. For instance, 75% recovery was achieved when 10% ethanol was present in a pCMV CAT plasmid formulation [DODAC/EPC/PEG-C14 (45:45:10), ±1:1, see, se8c233 in Table 1.

6. Evaluation of oligonucleotide association efficiency

The association efficiency of oligonucleotides in the formulation was evaluated using the ÷detergent method as described in Technical Report 131. The fluorometer was operated at excitation of 485 rnm with bandwidth 4 nm and emission of 530 nm with bandwidth 4 run. Fluorescence was measured using the time trace mode. Association efficiency of the oligonucleotide (or DNA) with the lipid in the formulation was evaluated by the accessibility of the fluorescent dye to the oligonucleotide and calculated as follows:

Formulation in the absence of fluorescent dye was used as the background reference. PicoGreen was used for the measurement of DNA association.

7. Evaluation of Oligonucleotide Encapsulation Efficiency Using DEAE Column Chromatography A 200 μl aliquot of the formulation containing about 10 μg oligonucleotide were eluted on a DEAE Sepharose CL-6B column with HBS. The amount of oligonucleotide recovered from the column was evaluated by OliGreen fluorescence assay as described above. To follow the lipid recovery after the column $^3$H-CHE was incorporated into the formulation. The oligonucleotide encapsulation efficiency was calculated as follows:

$$\text{encapsulation efficiency (\%)} = \left[\frac{\text{Oligo recovery (\%)}}{\text{Lipid recovery (\%)}}\right] \times 100 \quad (2)$$

C. Results

1. Efficiency of Oligonucleotide Extraction

Figure 3:
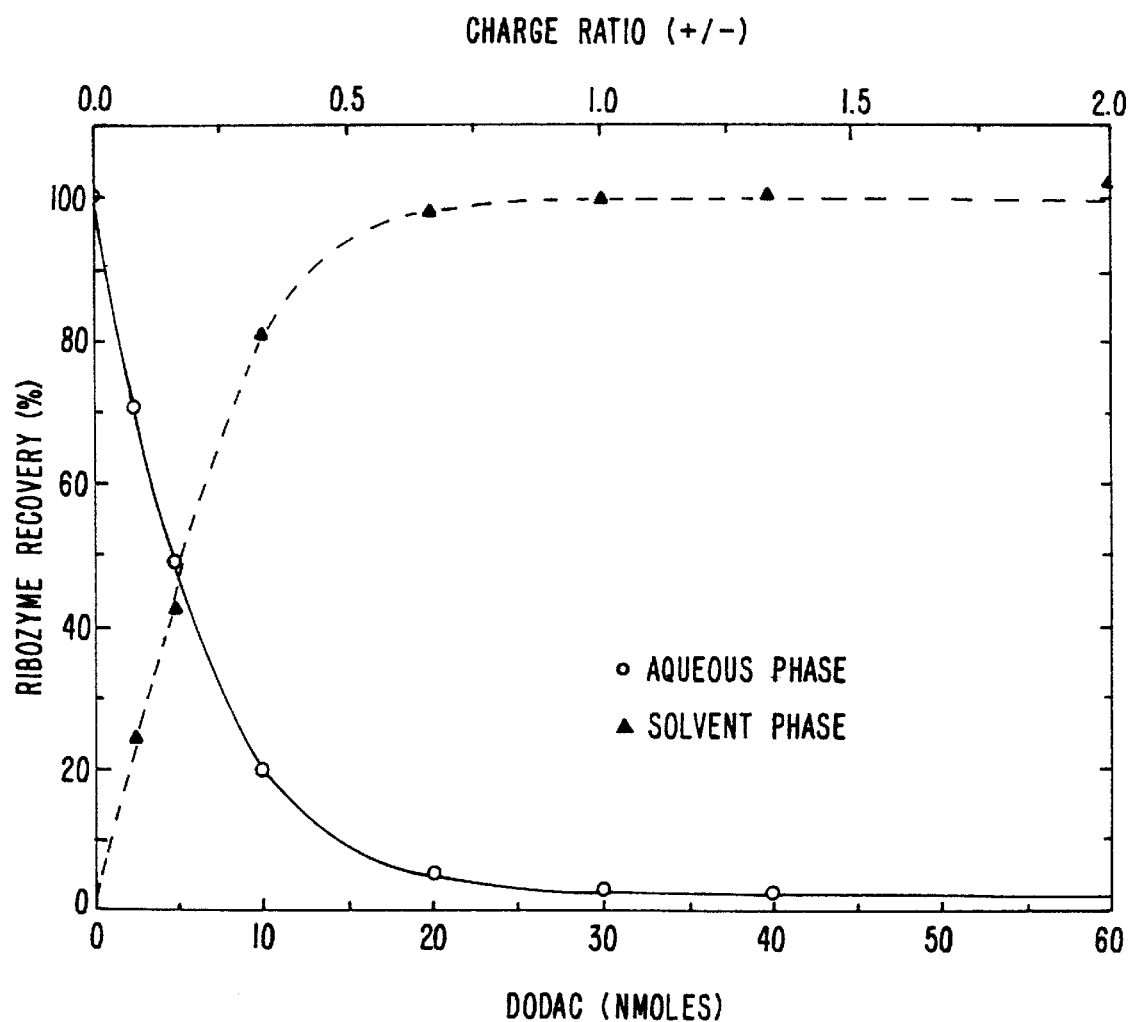
FIG. 3. Plots showing the efficiencies of the solvent extraction of ribozyme, R5356.15, into the solvent phase. Each sample contained 10$\mu$g of ribozyme. The amount of ribozyme recovered in the solvent and aqueous phases were shown as functions of cationic lipid concentration.

The efficiency of oligonucleotide extraction into the solvent phase appears to be very efficient as shown in FIG. 3 where the amount of ribozyme recovery (%) in the solvent phase and the aqueous phase are plotted as functions of DODAC amount or charge ratio (±). In this experiment the ribozyme (R5356.15) was fixed at 10μg including trace amount of $^{32}$P-ribozyme (3300 DPM/μg) and the lipid system used was DODAC/DOPE/PEG-Cer-C14 (45:45:10 mol. %). The results showed that over 80% of the ribozyme was observed in the solvent phase at charge ratio (±) of 0.33 and essentially 100% of the ribozyme was extracted into the solvent phase at charge ratio of 0.7 and higher.

2. TCS Size Distribution After Hydration The sizes of formulations after hydration varies from sample to sample. For ribozyme formulations with charge ratio of 1:1 the size varied from less than 200 nm (AU13R232) to as large as 500–600 nm (AU15R241). When the charge ratio was increased to 2:1 & 3:1 (±) the size decreased to range of 150–250 nm. Notice there are two samples contained no EPC but different amounts of oligonucleotide were used.

3. Reduction of Particle Size Distribution by Sonication

Figure 4A:
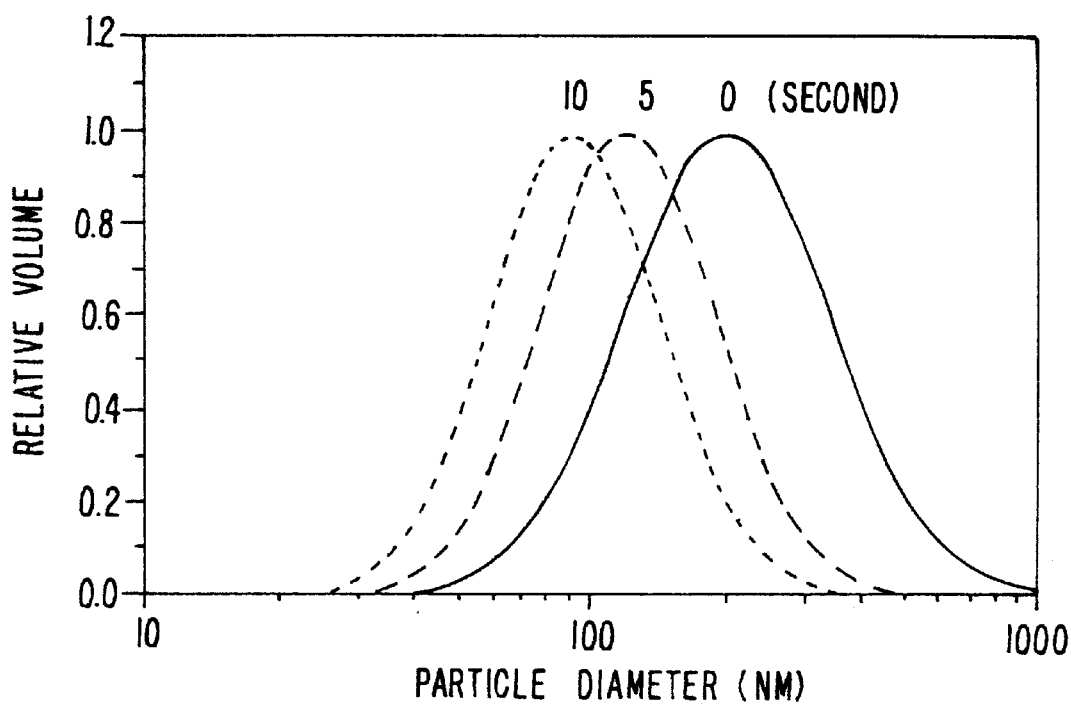
FIG. 4. An example of the size distribution for a formulation of oligo-lipid particle before and after sonication.
Figure 4B:
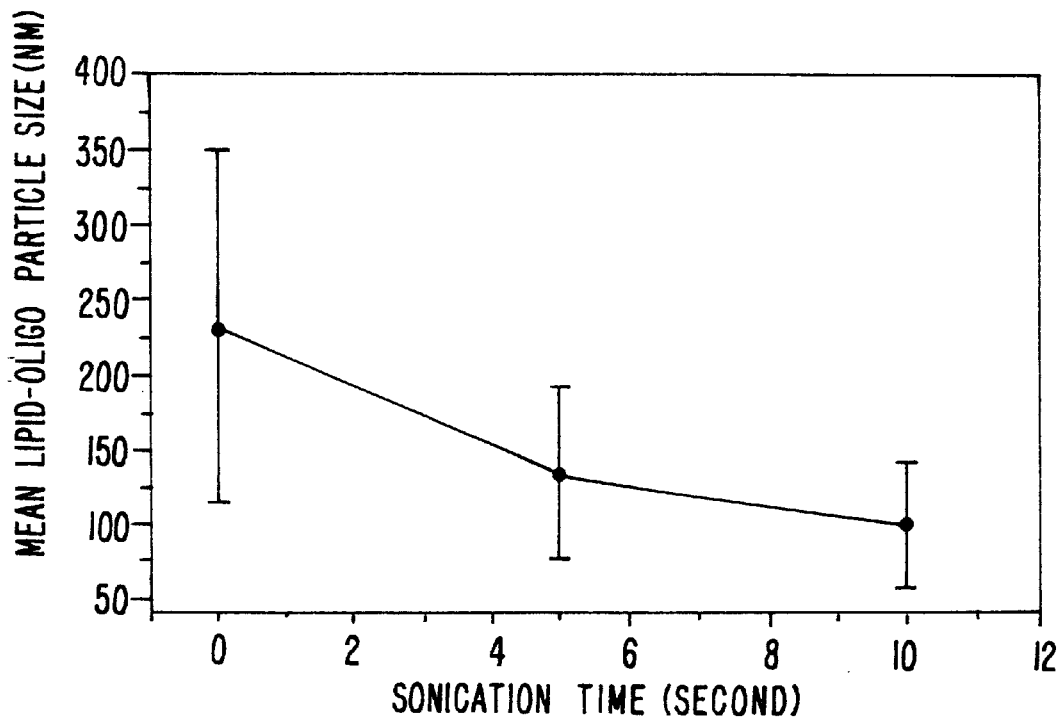

The size of formulations after direct hydration of the dry lipid/oligo complexes were all large (in the range of 300–700 nm) even for formulations containing 10 mol. % PEG-Cer-C14 (see, Table 1). Formulations were, therefore, subject to brief sonication or extrusion through 100 nm filters to reduce the particle size distributions. The effect of sonication on TCS size distributions is shown in FIG. 4 for a typical system composed of ISIS 1082 and DODAC/EPC/PEG-Cer-C14 (45:45:10 mol. %) with a charge ratio of 1:1. The initial mean particle size was 232±120 nm (350±180 as vesicles) after hydration in HBS (see, Table 1.B. for details). The sizes were reduced to 135±58 run (220±95 for vesicles) and 103±44 nm (175±75 for vesicles), respectively, after 5 seconds and 10 seconds sonication. Further sonication appeared to have weak effect on the size of the formulations. Similar results were observed for R5356.15 system. More detailed results are summarized in Table 1.-

$$\text{Association efficiency} = \left[1 - \frac{\text{Fluorescence intensity of (formation} + \text{OliGreen)}}{\text{Fluorescence intensity of (formulation} + \text{OliGreen} + 40 \text{ mM OPG)}}\right] \times 100 \quad (1)$$

4. Effect of Sonication on the Integrity of Oligonucleotides

Figure 5:
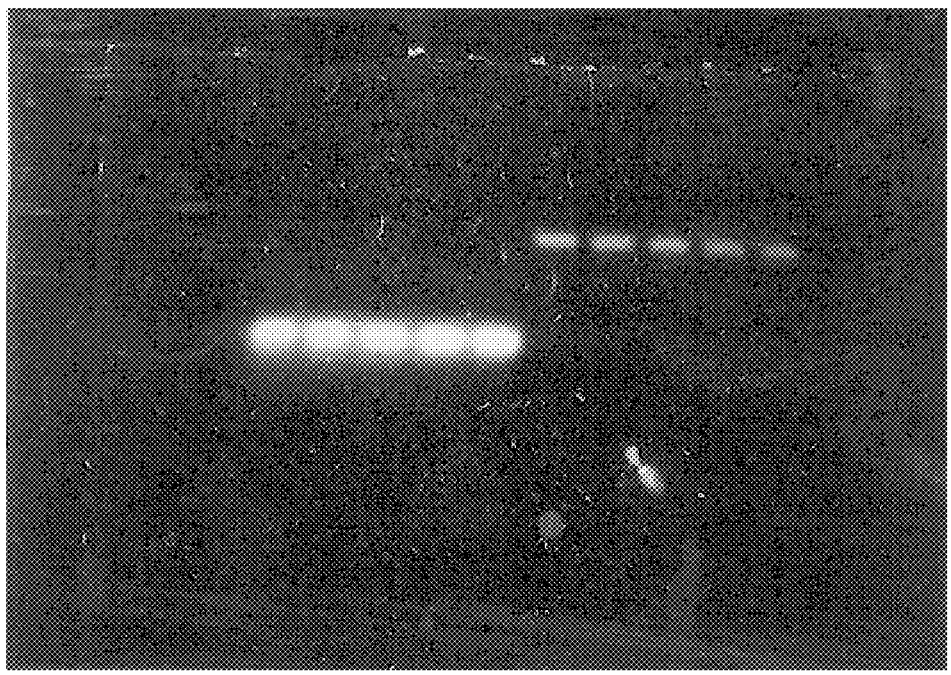
FIG. 5. DEAE ion exchange chromatography showing the profile of lipid and ISIS 1082 recovery in the eluted fractions. 50 $\mu$g ISIS 1082 and 1.15 mg lipid (DODAC/EPC/PEG-C14, 45:45:10 mol %). The lipid was followed by a $^3$H-CHE tracer and the antisense was determined by Oli-Green assay. The total lipid and oligonucleotide recoveries were 90% and 60% respectively. More than 85% of the total recovered lipid and oligonucleotides were recovered in the second fraction.

In order to insure that sonication did not degrade oligonucleotides, the following test was carried out. Two micrograms of either antisense (ISIS 1082) or ribozyme (R5356.15) were diluted to 4 μl/mL and the solutions were then subjected to sonication for various lengths of time (0 to 60 sec) at the lowest power (position 1). The integrity of the oligonucleotides was examined using acrylamide gel. As shown in FIG. 5, both the ribozyme and the antisense retained their integrity even after 60 seconds sonication. On the other hand complete degradation of plasmid DNA was observed after 10 seconds sonication (results not shown).

5. Evaluation of oligonucleotide encapsulation by DEAE column

Figure 6:
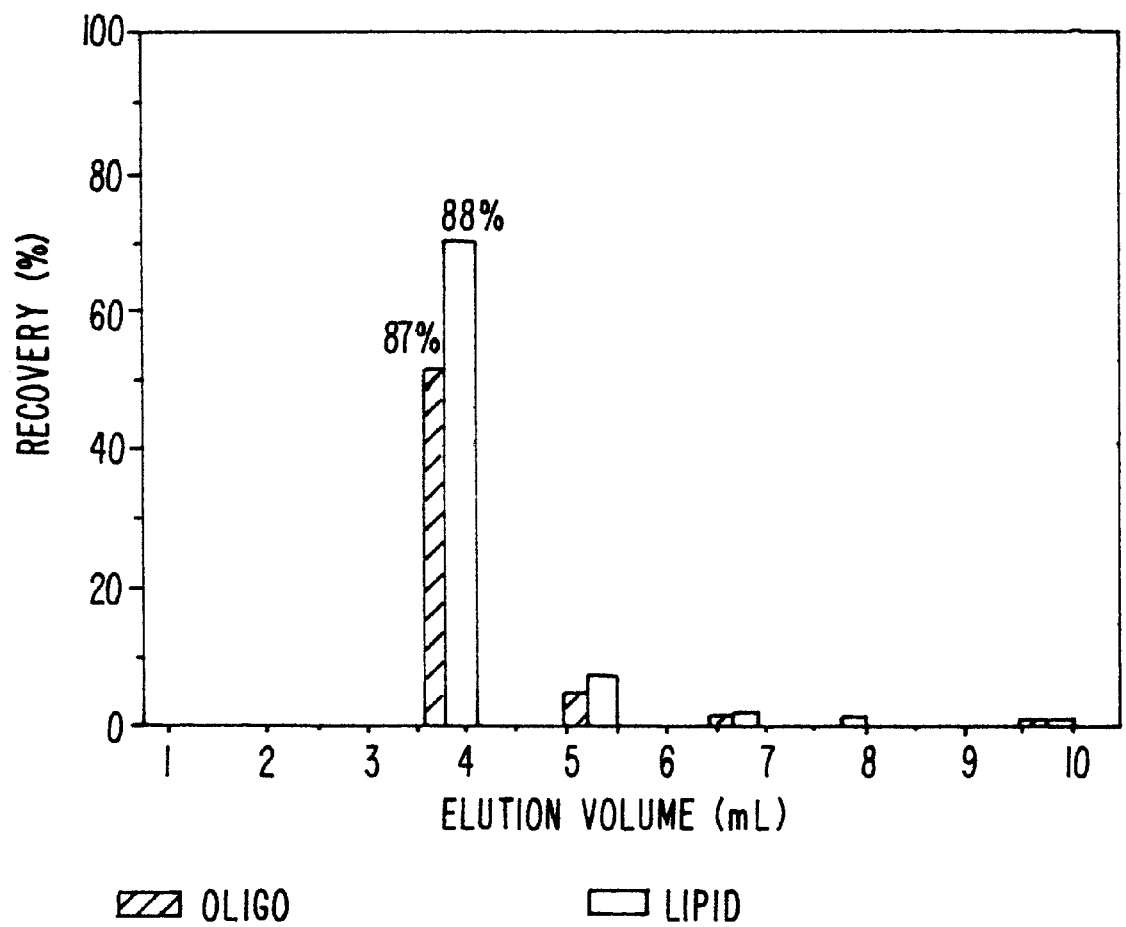
FIG. 6. Electrophoresis gel study showing that oligonucleotides were not degraded by sonication.

The encapsulation efficiency of oligonucleotide or DNA was evaluated by DEAE ion exchange column chromatography. After sonication formulation was loaded to a DEAE Sepharose CL-4B ion exchange column (1.5×10 cm column with 5 cm to remove non-encapsulated oligonucleotides. The column was eluted with HBS and 6 fractions (1.5–2 mL each) were collected. FIG. 6 presents the elution profile of both lipid and antisense for a formulation composed of 50 μg of ISIS 1082 and 1.15 mg of DODAC/DOPE/PEG-Cer-C14 (45:45:10 mol. %). The lipid was followed by a $^3$H-CHE tracer and the antisense was determined by OliGreen assay. The results shown a lipid recovery of 90% and an oligonucleotide recovery of 60% for the loaded formulation. Moreover, about 88% of the total recovered lipid and oligonucleotides were recovered in the second fraction. The encapsulation efficiency was calculation by equation 2.

D. Discussion

A novel Solvent Extraction and Direct Hydration method is provided for the preparation of lipid based TCS for the delivery of antisense molecules, ribozymes and DNA molecules into cells. This method involves the generation of hydrophobic polynucleic acids complexes with cationic lipids in organic solvent with helper non-cationic lipids (e.g., neutral lipids) and PEG-containing lipids. TCS formulations were then prepared by hydration of the lipid-nucleic acid complexes in HBS. Sonication (for oligonucleotides) or extrusion (for plasmid) were used to reduce the size of the formulations. In conclusion, the formulations prepared by SEDH method have excellent characteristics. Moreover, the biggest advantages of this method over existing methods are that they are simple, time efficient (can be completed in 5–8 hrs) and they achieve high encapsulation efficiencies.

The concepts of "association" and "encapsulation" are used herein for different purposes. Fluorescence assay using OliGreen/PicoGreen (±Triton X-100) cannot distinguish the entrapped oligonucleotide/DNA within the TCS particles and the oligonucleotide/DNA bound at the surface of the liposomes; therefore, the term "association efficiency" is used to describe the percentage of oligonucleotide/DNA that is not accessible to the fluorescent reagent vs. the total oligonucleotide/DNA in the system (see, equation 1). The term of "encapsulation efficiency" is used to measure the percentage of oligonucleotide/DNA entrapped within the TCS. It is believed that the bound oligonucleotides/DNA on the surface were mostly, if not completely, removed by passing the formulation through a DEAE column. Therefore, the percentage recovery of oligonucleotide/DNA from DEAE column (see, equation 2) is described as encapsulation efficiency.

The high efficiency for oligonucleotide extraction into the solvent phase is comparable with that observed for DNA system, indicating that the nature of interaction of cationic lipids with small oligonucleotides (20-mer for the antisense and 29-mer for the ribozyme) and DNA (several thousands of base pairs) is similar.

At a charge ratio of 0.7/1 (±), essentially 100% of the oligonucleotide is found in the solvent phase for all antisense and ribozyme systems regardless of the non-cationic lipids (e.g., neutral lipids) used. However, the observed encapsulation efficiencies for oligonucleotides and DNA in each of these formulations varies depending on the charge ratio and the type of neutral lipid involved. The near 100% encapsulation efficiencies for EPC-based antisense formulation at charge ratio of 1:1 (±) indicates that the antisense-lipid complexes formed in the solvent were well preserved during the removal of solvent and the hydration process. In comparison, the encapsulation observed for DOPE-based antisense formulations were in the range of 50–70%, which is still excellent compared with that obtained using the detergent dialysis method in which 20–50% encapsulation is typically observed.

In addition, the encapsulation efficiencies observed for the ribozyme formulations are generally lower than those observed for the antisense formulations when the same lipid composition was used. It is thought that this may be attributed to the difference in the secondary structures between antisense and ribozyme.

Encapsulation efficiency is affected by the type of non-cationic lipids used. As studied using the antisense formulations, DOPE-based formulations exhibited lower encapsulation than the EPC-based formulation. The reason for such difference is unclear. However, it might be explained by the differences in the biophysical properties between PC and PE. PC is relatively easy to hydrate and PE in comparison is more difficult to hydrate. The tendency of DOPE to form non-lamellar structure may also play a role. In addition, DOPE, when present in high concentration, influences the interaction between oligonucleotides and DODAC as pointed out by Reimer, et al., supra (1995). Although DOPE did not affect the interaction of oligonucleotides with DODAC in the extraction stage at the concentration used, it might have done so when the lipid was concentrated up during the removal of solvent and/or in the hydration stage.

JL4A341 (45 mol % DODAC) and JL4A342 (25 mol % DODAC) are the only formulations that contained the fusogenic lipid, DOPE. Both formulations exhibited very good encapsulation efficiency although lower than that for the EPC containing formulation. It is very interesting to note that the encapsulation efficiencies decreased from 76% to 53% when the DOPE concentration was increased from 45 mol % to 65 mol % (the DODAC/DNA ratio remained unchanged), which corresponds to a 160% increase in DOPE weight (as well as an 80% increase in PEG-C14). This finding suggests that DOPE (and/or PEG) influences the interaction between DNA and DODAC.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A method for the preparation of a lipid-nucloic acid particle, said method comprising:

(a) contacting a nucleic acid with a solution comprising a non-cationic lipid and a cationic lipid to form a lipid-nucleic acid mixture, said solution comprising about 15–35% water and about 65–85% of an organic solvent;

(b) removing the aqueous portion of said lipid-nucleic acid mixture to form a non-aqueous lipid-nucleic acid mixture;

(c) removing the organic solvent portion from said non-aqueous lipid-nucleic acid mixture to form a lipid-nucleic acid complex in the form of a film; and (d) hydrating said lipid-nucleic acid complex to form said nucleic acid-lipid particle.

2. The method in accordance with claim 1, wherein said nucleic acid is a plasmid.

3. The method in accordance with claim 1, wherein said nucleic acid is an antisense molecule.

4. The method in accordance with claim 1, wherein said nucleic acid is a ribozyme.

5. The method in accordance with claim 1, wherein said non-cationic lipid is a neutral lipid.

6. The method in accordance with claim 1, wherein said non-cationic lipid is a member selected from the group consisting of diacylphosphatidylcholines, diacylphosphatidylethanolamines, ceramides, sphingomyelins, cephalins, and cerebrosides.

7. The method in accordance with claim 1 wherein said non-cationic lipid is a diacylphosphatidylcholine.

8. The method in accordance with claim 7, wherein said diacylphosphatidylcholine is a member selected from the group consisting of dioleoylphosphatidylcholine, dipalmitoylphosphatidylcholine and dilinoleoylphosphatidylcholine.

9. The method in accordance with claim 7, wherein said diacylphosphatidylcholine is egg yolk phosphatidylcholine (EYPC).

10. The method in accordance with claim 1, wherein said non-cationic lipid is a diacylphosphatidylethanolamine.

11. The method in accordance with claim 10, wherein said diacylphosphatidylethanolamine is a member selected from the group consisting of dioleoylphosphatidylethanolamine and palmitoyloleoylphosphatidylethanolamine.

12. The method in accordance with claim 1, wherein said cationic lipid is a member selected from the group consisting of 3β-(N-(N',N'-dimethylaminoethane)carbamoyl) cholesterol (DC-Chol), N,N-distearyl-N,N-dimethylammonium bromide (DDAB), N-(1,2-dimyristyloxyprop-3-yl)-N,N-dimethyl-N-hydroxyethyl ammonium bromide (DMRIE), diheptadecylamidoglycyl spermidine (DOGS), N-(1-(2,3-dioleyloxy)propyl)-N-(2-(sperminecarboxamido)ethyl)-N,N-dimethylammonium trifluoroacetate (DOSPA), N-(1-(2,3-dioleoyloxy)propyl)-N,N,N-trimethylammonium chloride (DOTAP), N-(1-(2,3-dioleyloxy)propyl)-N,N,N-trimethylammonium chloride (DODAC) and N,N-dioleyl-N,N-dimethylammonium chloride (DOTMA).

13. The method in accordance with claim 12, wherein said cationic lipid is DODAC.

14. The method in accordance with claim 12, wherein said cationic lipid is DOTAP.

15. The method in accordance with claim 1, wherein said solution further comprises a polyethyleneglyocol (PEG)-lipid conjugate.

16. The method in accordance with claim 15, wherein said PEG-lipid conjugate is a PEG-phosphatidylethanolamine conjugate.

17. The method in accordance with claim 16, wherein said phosphatidylethanolamine is a member selected from the group consisting of dimyristoylphosphatidylethanolamine, dipalmitoylphosphatidylethanolamine, dioleoylphosphatidylethanolamine and distearoylphosphatidylethanolamine.

18. The method in accordance with claim 15, wherein said PEG has a molecular weight ranging from about 200 to 10,000.

19. The method in accordance with claim 15, wherein said PEG has a molecular weight ranging from about 1,000 to 8,000.

20. The method in accordance with claim 15, wherein said PEG has a molecular weight ranging from about 2,000 to 6,000.

21. The method in accordance with claim 15, wherein PEG-lipid conjugate is a PEG-ceramide (Cer) conjugate.

22. The method in accordance with claim 21, wherein said PEG-Cer conjugate comprises a fatty acid group having from 6 to 20 carbon atoms.

23. The method in accordance with claim 21, wherein said PEG-Cer conjugate is selected from the group consisting of PEG-Cer-$C_8$, PEG-Cer-$C_{14}$ and PEG-Cer-$C_{20}$.

24. The method in accordance with claim 21, wherein said PEG-Cer conjugate is PEG-Cer-$C_8$.

25. The method in accordance with claim 21, wherein said PEG-Cer conjugate is PEG-Cer-$C_{14}$.

26. The method in accordance with claim 21, wherein said PEG-Cer conjugate PEG-Cer-$C_{20}$.

27. The method in accordance with claim 15, wherein said PEG-lipid conjugate is present at a concentration ranging from about 0.5 mole percent to about 50 mole percent.

28. The method in accordance with claim 1, wherein said solution further comprises cholesterol.

29. The method in accordance with claim 28, wherein said cholesterol is present at a concentration ranging from about 0.2 mole percent to about 50 mole percent.

30. The method in accordance with claim 1, wherein said solution of step (a) is a monophase solution.

31. The method in accordance with claim 1, wherein said organic solvent is a member selected from the group consisting of methanol, chloroform, methylene chloride, ethanol, diethyl ether, and combinations thereof.

32. The method in accordance with claim 1, wherein said organic solvent is a mixture of methanol and chloroform.

33. The method in accordance with claim 1, wherein said hydration step comprises contacting said lipid-nucleic acid complex with a buffer to form said lipid-nucleic acid complex.

34. The method in accordance with claim 20, wherein said buffer is a member selected from the group consisting of HBS, HEPES, PBS, EGTA, citrate, tris EDTA and tris buffer.

35. The method in accordance with claim 1, wherein said organic solvent portion is removed by evaporation.

36. The method in accordance with claim 1, wherein the size of said lipid-nucleic acid particle ranges from about 200 to about 500 nm.

37. The method in accordance with claim 1, further comprising the step of sizing said lipid-nucleic acid particle.

38. The method in accordance with claim 1, wherein greater than 60% of said nucleic acid is encapsulated into said lipid-nucleic acid particle.

39. The method in accordance with claim 1, wherein greater than 70% of said nucleic acid is encapsulated into said lipid-nucleic acid particle.

40. The method in accordance with claim 1, wherein greater than 80% of said nucleic acid is encapsulated into said lipid-nucleic acid particle.

41. The method in accordance with claim 1, wherein greater than 90% of said nucleic acid is encapsulated into said lipid-nucleic acid particle.

42. The method in accordance with claim 1, wherein greater than 95% of said nucleic acid is encapsulated into said lipid-nucleic acid particle.

43. The method in accordance with claim 1, wherein said non-cationic lipid is present at a concentration ranging from about 20 mole percent to about 95 mole percent.

44. The method in accordance with claim 1, wherein said cationic lipid is present at a concentration ranging from about 5 mole percent to about 80 mole percent.

45. A method for introducing a nucleic acid in a cell, said method comprising:
(a) preparing a lipid-nucleic acid particle in accordance with the method of claim 1; and
(b) contacting said cell with said lipid-nucleic acid particle for a period of time sufficient to introduce the nucleic acid into said cell.

46. The method in accordance with claim 45, wherein said lipid-nucleic acid particle comprises a plasmid.

47. The method in accordance with claim 45, wherein said lipid-nucleic acid particle comprises an antisense molecule.

48. The method in accordance with claim 46, wherein said lipid-nucleic acid particle comprises a ribozyme.

49. The method in accordance with claim 45, wherein said lipid-nucleic acid particle comprises EYPC, DODAC, a ribozyme and a PEG-Cer conjugate.

50. The method in accordance with claim 49, wherein said lipid-nucleic acid particle further comprises cholesterol.

51. The method in accordance with claim 45, wherein said lipid-nucleic acid particle comprises EYPC, DOTAP, a ribozyme and a PEG-Cer conjugate.

52. The method in accordance with claim 51, wherein said lipid-nucleic acid particle further comprises cholesterol.

* * * * *